(12) United States Patent
Dhanoa et al.

(10) Patent No.: US 7,598,265 B2
(45) Date of Patent: Oct. 6, 2009

(54) COMPOSITIONS AND METHODS FOR TREATING CNS DISORDERS

(75) Inventors: Dale S. Dhanoa, Wakefield, MA (US); Oren Becker, Mevaseret Zion (IL); Silvia Noiman, Herzliya (IL); Pradyumna Mohanty, Woburn, MA (US); Dongli Chen, Chestnut Hill, MA (US); Mercedes Lobera, Concord, MA (US); Laurence Wu, Woburn, MA (US); Yael Marantz, Kadima (IL); Boaz Inbal, Kfar Shmuel (IL); Alexander Heifetz, Bnei-Brak (IL); Shay Bar-Haim, Netanya (IL); Sharon Shacham, Alfey Menashe (IL)

(73) Assignee: Epix Delaware, Inc., Lexington, MA (US)

( * ) Notice: Subject to any disclaimer, the term of this patent is extended or adjusted under 35 U.S.C. 154(b) by 299 days.

(21) Appl. No.: 11/271,019

(22) Filed: Nov. 10, 2005

(65) Prior Publication Data

US 2006/0234998 A1    Oct. 19, 2006

(51) Int. Cl.
*A61K 31/44* (2006.01)
*C07D 513/02* (2006.01)

(52) U.S. Cl. .................... 514/301; 546/114
(58) Field of Classification Search .............. 546/114; 514/301
See application file for complete search history.

(56) References Cited

U.S. PATENT DOCUMENTS

| | | |
|---|---|---|
| 3,069,412 A | 12/1962 | Roberts et al. |
| 3,658,807 A | 4/1972 | Schmidt et al. |
| 4,146,716 A | 3/1979 | Cox et al. |
| 4,316,020 A | 2/1982 | Reissenweber et al. |
| 5,155,155 A | 10/1992 | Jurlaro et al. |
| 5,219,864 A | 6/1993 | Suzuki et al. |
| 5,227,387 A | 7/1993 | Dreikorn et al. |
| 5,236,917 A | 8/1993 | Dunlap et al. |
| 5,371,074 A | 12/1994 | Dunlap et al. |
| 5,378,679 A | 1/1995 | Nuebling et al. |
| 5,571,815 A | 11/1996 | Schaper et al. |
| 5,591,751 A | 1/1997 | Fujioka et al. |
| 5,593,943 A | 1/1997 | Nuebling et al. |
| 5,596,012 A | 1/1997 | Dunlap et al. |
| 5,650,422 A | 7/1997 | Dunlap et al. |
| 5,753,673 A | 5/1998 | Ohuchi et al. |
| 5,798,451 A | 8/1998 | von Deyn et al. |
| 5,874,432 A | 2/1999 | Dunlap et al. |
| 5,972,841 A | 10/1999 | von Deyn et al. |
| 6,103,903 A | 8/2000 | Cai et al. |
| 6,159,962 A | 12/2000 | Steiner et al. |
| 6,187,788 B1 | 2/2001 | Furuya et al. |
| 6,222,034 B1 | 4/2001 | Steiner et al. |
| 6,232,320 B1 | 5/2001 | Stewart et al. |
| 6,300,333 B1 | 10/2001 | Schaper et al. |
| 6,340,759 B1 | 1/2002 | Ueno et al. |
| 6,596,727 B1 | 7/2003 | Schaper et al. |
| 6,924,283 B2 | 8/2005 | Thorarensen |
| 7,030,240 B2 | 4/2006 | Dhanoa et al. |
| 7,119,205 B2 | 10/2006 | Iyengar et al. |
| 7,153,858 B2 | 12/2006 | Dhanoa et al. |
| 7,407,966 B2 | 8/2008 | Dhanoa et al. |
| 2002/0028782 A1 | 3/2002 | Castelhano et al. |
| 2004/0138238 A1 | 7/2004 | Dhanoa et al. |
| 2005/0049243 A1 | 3/2005 | Ballard et al. ............ 514/221 |
| 2005/0065176 A1 | 3/2005 | Field et al. ............... 514/291 |
| 2005/0137142 A1 | 6/2005 | Schulz et al. ............. 514/19 |
| 2005/0222175 A1 | 10/2005 | Dhanoa et al. |
| 2005/0222176 A1 | 10/2005 | Dhanoa et al. |
| 2006/0084805 A1 | 4/2006 | Dhanoa et al. |
| 2006/0084806 A1 | 4/2006 | Sridharan et al. |
| 2006/0205737 A1 | 9/2006 | Becker et al. |
| 2007/0004742 A1 | 1/2007 | Dhanoa et al. |
| 2007/0173487 A1 | 7/2007 | Saha et al. |

FOREIGN PATENT DOCUMENTS

| | | |
|---|---|---|
| EP | 0447891 | 9/1991 |
| EP | 0503844 | 9/1992 |
| EP | 0503844 A | 9/1992 |
| EP | 0505058 | 9/1992 |
| EP | 0505058 A | 9/1992 |
| EP | 0 710 662 A1 | 5/1996 |
| EP | 1 018 513 A2 | 7/2000 |
| EP | 1 018 513 A3 | 7/2000 |
| EP | 0 710 662 B1 | 4/2001 |
| EP | 1229025 | 8/2002 |
| EP | 1325921 | 7/2003 |
| EP | 1325921 A | 7/2003 |
| EP | 1 018 513 B1 | 2/2006 |
| GB | 2295387 | 5/1996 |
| JP | 11 130777 A | 5/1999 |
| WO | WO 94/12176 | 6/1994 |
| WO | WO 94/22871 | 10/1994 |
| WO | WO 00/64441 A | 11/2000 |
| WO | WO 01/14333 | 3/2001 |

(Continued)

OTHER PUBLICATIONS

Buchstaller, H.P., et al., "Thieno[2,3-b]pyridinones as Antagonists on the Glycine Site of the N-methyl-D-aspartate Receptor-Binding Studies, Molecular Modelling and Structure-Activity-Relationships", Scientia Pharmazeutica, 68, 3-14 (2000).

(Continued)

*Primary Examiner*—Janet L. Andres
*Assistant Examiner*—Raymond Covington
(74) *Attorney, Agent, or Firm*—Goodwin Procter LLP

(57) ABSTRACT

The invention generally relates to thienopyridinone 5-HT$_4$ receptor modulators, and in particular the use of these compounds and their pharmaceutical compositions, e.g., in the treatment, modulation and/or prevention of physiological conditions associated with serotonin action, such as in treating Alzheimer's disease, cognition disorders, depression, and anxiety.

25 Claims, 2 Drawing Sheets

FOREIGN PATENT DOCUMENTS

| | | |
|---|---|---|
| WO | WO 01/25218 | 4/2001 |
| WO | WO 02/102797 | 12/2002 |
| WO | WO 2004/014850 | 2/2004 |
| WO | WO 2004/017950 | 3/2004 |
| WO | WO 2004/030629 | 4/2004 |
| WO | WO 2004/034963 | 4/2004 |
| WO | WO 2004/089312 | 10/2004 |
| WO | WO 2005/121151 | 12/2005 |
| WO | WO2005/121151 A | 12/2005 |
| WO | WO 2006/041985 | 4/2006 |
| WO | WO 2007/058805 | 5/2007 |
| WO | WO 2008/002539 | 1/2008 |
| WO | WO 2008/045558 | 4/2008 |
| WO | WO 2008/060632 | 5/2008 |

OTHER PUBLICATIONS

Lamirault, L., et al., "Combined Treatment with Galanthaminium Bromide, a New Cholinesterase Inhibitor, and RS 67333, a Partial Agonist of 5-HT4 Receptors, Enhances Place and Object Recognition in Young Adult and Old Rats," Progress in Neuro-Psychopharmacology & Biological Psychiatry 27 (2003) 185-195.
Moser, Paul C., et al., "SL65.0155, A Novel 5-Hydroxytryptamine4 Receptor Partial Agonist with Potent Cognition-Enhancing Properties," The Journal of Pharmacology and Experimental Therapeutics, 302:731-741, 2002.
Science IP Search, Apr. 30, 2004.
Science IP Search, May 11, 2004.
Stachel, Hans-Dietrich, et al., "Derivatives of Oxalyldimalonic Acid," 1995.
Suzuki, M., "Synthesis and Evaluation of Novel 2-Oxo-1,2-dihydro-3-Quinolinecarboxamide Derivatives as Potent and Selective Serotonin 5-HT4 Receptor Agonists," Chem Pharm. Bull., 49(1) 29-39, 2001.
Buchheit et al. J. Med. Chem., 38(13):2326-2330 (1995).
Buchheit et al. J. Med. Chem., 38(13):2331-2338 (1995).
Kaumann, A.J. Naunyn-Schmiedeberg's Arch. Pharmacol., 342:619-622 (1990).
Moser et al. J. Pharmacol. Exp. Ther., 302(2):731-741 (2002).
Abenhaim et al. N. Engl. J. Med., 335(9):609-616 (1996).
Barker et al., Journal of Chemical Research, Synopses, 1985 (7) 214-15.
Brea et al. J. Med. Chem., 45:54-71 (2002).
Coppola et al., Journal of Organic Chemistry, 1976 (41) 825-831.
Database Caplus on STN, Accession No. 1999:783937, Castelhano et al., WO 99/62518 A1, Cadue Pharmaceuticals Corp. Dec. 9, 1999.
Database Caplus on STN, Accession No. 2000:806616 Horvath, et al., Neurogen Corporation. 6,147,085, Nov. 14, 2000.
Doggrell, Sheila A., Expert Opin. Investig. Drugs, 2003 (12) 805-823.
Farber et al. N. Engl. J. Med., 351(16):1655-1665 (2004).
Fishman Chest, 114(3):242S-247S (1998).
Fitzgerald et al. Mol. Pharmacol., 57:75-81 (2000).
Gordon W. Gribble, Sodium Borohydride in Carboxylic Acid Media: A Phenomenal Reduction System, Chemical Society Reviews, 1998 (27) 395-40.
Hutchins, R.O., et al., J. Org. Chem., 1977 (42) 82-91.
Hwang et al., Arch. of Pharm. Res., 2001, 24(4), 270-275.
International Search Report for PCT/US2003/23539 mailed Jul. 23, 2004.
International Search Report for PCT/US2004/09944 mailed Mar. 1, 2005.
International Search Report for PCT/US2005/035935 mailed May 12, 2006.
International Search Report for PCT/US2005/034862 mailed Jan. 24, 2006.
International Search Report for PCT/US2005/17121 mailed Apr. 4, 2006.
International Search Report for PCT/US2006/043140 mailed Aug. 16, 2007.
Jerry March in Advanced Organic Chemistry 4th Edition, 1992, by John Wiley & Sons: New York, pp. 378-383.
Kennett et al. Neuropharmacol., 36(2):233-239 (1997).
Kursar et al. Mol. Pharmacol., 46(2):227-234 (1994).
Kuryshev et at J. Pharmacol. Exp. Ther., 295(2):614-620 (2000).
Launay et al. Nat. Med., 8(10):1129-1135(2002).
MacLean Trends Pharmacol. Sci., 20(12):490-495 (1999).
Manivert et al. J. Biol. Chem., 277(19):17170-17178 (2002).
Marcos et al. Circ. Res., 94:1263-1270 (2004).
Nauser et al. Am. Fam. Physician, 63(9):1789-1798 (2001).
Nebigil et al. Proc. Natl. Acad. Sci. U.S.A., 97(6):2591-2596 (2000).
Poissonnet et al. Mini-Rev. Med. Chem., 4(3):325-330 (2004).
Recanatini, M., et al., "Acetylcholinesterase Inhibitors in the Context of Therapeutic Strategies to Combat Alzheimer's Disease," Expert Opinion on Therapeutic Patents, Ashley Publications, GB, vol. 12, No. 12, 2002, 1853-1865.
Rich et al. Chest, 117(3):870-874 (2000).
Rothman et al. Circulation, 102:2836-2841 (2000).
Setola et al. Mol. Pharmacol., 63(6):1223-1229 (2003).
Takashi et al., Bioorganic & Medicinal Chemistry Letters, 2002 (12) 2427-2430.
Teoh et al., "Hypoxia Enhances 5-HT2B Receptor Response and Expression the Rat Pulmonary Artery", Abstract only, International Conference of the American Thoracic Society, San Diego (May 24, 2005).
Ullmer et al. Br. J. Pharmacol., 117(6):1081-1088 (1996).
Witchel et al. FEBS Lett., 512(1-3):59-66 (2002).
Witchel et al. J. Clin. Psychopharmacol., 23(1):58-77 (2003).
Yamada et al. Eur. J. Pharmacol., 406(1):153-157 (2000).

COMPOSITIONS AND METHODS FOR TREATING CNS DISORDERS

RELATED APPLICATIONS

This application claims the benefit of priority under 35 U.S.C. 119(e) to copending U.S. application Ser. No. 10/955,434, filed on Sep. 30, 2004, and Ser. No. 10/960,769, filed on Oct. 7, 2004; the entire contents of which are incorporated herein by reference.

FIELD OF THE INVENTION

The invention generally relates to the field of 5-$HT_4$ receptor modulators, e.g., agonists, partial agonists, inverse agonists, antagonists, and more particularly to new thienopyridinone compounds, and in particular the use of these compounds with (acetyl)cholinesterase inhibitors and in pharmaceutical compositions, e.g., in the treatment, modulation and/or prevention of physiological conditions associated with serotonin action, such as in treating Alzheimer's disease, cognition disorders, depression, and anxiety.

BACKGROUND OF THE INVENTION

The serotonergic neural system of the brain has been shown to influence a variety of physiologic functions which manifest themselves in a variety of disorders such as Alzheimer's disease, cognition disorders, anxiety, migraine, and ischemic stroke. 5-HT receptor modulators e.g., agonists, partial agonists, inverse agonists and antagonists, and/or selective serotonin reuptake inhibitors (SSRIs) such as fluoxetine, paroxetine, fluvoxamine, sertraline, lorazepam, imipramine, citalopram, and nortriptyline, may be used for the treatment of the above conditions, as well as for neuropathological disorders including Parkinson's disease. They also intervene in the regulation of the cerebral circulation and thus represent effective agents for controlling migraine. They are also suitable for the prophylaxis and control of the effects of occurrences of cerebral infarct (Apoplexia cerebri) such as stroke or cerebral ischemia.

The 5-$HT_4$ receptors represent a member of the family of receptors with seven transmembrane (7TM) domains coupled to a G-protein which is positively coupled to adenylate cyclase. The 5-$HT_4$ receptors are expressed in a wide variety of tissues, including the human brain and the rodent brain, the human, dog, pig and rodent gastro-intestinal tract, and the pig and human heart. In the mammalian brain, the 5-$HT_4$ receptors contribute to dopamine secretion and regulate learning and long-term memory via the modification of acetylcholine release. In the peripheral tissues, the 5-$HT_4$ receptors have proven to regulate gastro-intestinal tract motility, intestinal electrolyte secretion, adrenal secretion of corticosteroids, bladder contraction and atrium contractility.

The 5-$HT_4$ receptors are involved in a wide variety of central and peripheral disorders, including cardiac arrhythmias and neurodegenerative disorders and more specifically Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

The development of 5-$HT_4$ receptor modulators, e.g., agonists, partial agonists, inverse agonists and antagonists, may have therapeutic applications in the central nervous system for treating neuropsychiatric disorders associated with a dysfunction of the central dopaminergic system, such as Parkinson's disease, or for treating amnesic deficiencies as presented in patients suffering from Alzheimer's disease.

SUMMARY OF THE INVENTION

The present invention relates to the use of new compositions which include 5-$HT_4$ modulators, e.g., agonists, partial agonists, inverse agonists and antagonists, and/or SSRIs, for treating, preventing or curing Alzheimer's disease, memory conditions, cognition disorders, and depression; and cholinesterase or acetylcholinesterase inhibitors. The invention features a first compound which is a 5-$HT_4$ modulator; in an embodiment, such compounds include those having the formula

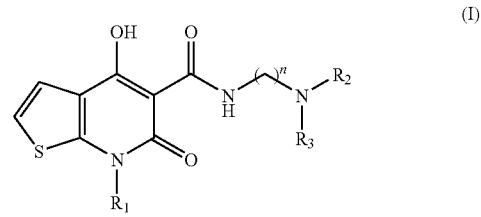

(I)

wherein $R_1$ may be a ($C_1$-$C_8$) branched or unbranched alkyl; a ($C_1$-$C_8$) substituted or unsubstituted carbocyclic ring; branched or unbranched haloalkyl, a substituted or unsubstituted aryl or heteroaryl ring, or a substituted or unsubstituted $(CH_2)_p$-aryl or $(CH_2)_p$-heteroaryl ring, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof. The amount of either first or second compound is present in an amount, which if administered alone, does not substantially enhance memory.

$R_1$ may be a ($C_1$-$C_8$) alkyl, e.g., methyl, ethyl, isopropyl, n-propyl, n-butyl or isobutyl; $R_2$ and $R_3$ taken together form a substituted or unsubstituted piperidine (N-containing six-membered cyclic ring); and n is 3. In another embodiment, the branched or unbranched haloalkyl group contains a halogen atom, e.g., F, Cl, Br, or I. A particularly useful 5-$HT_4$ compound for use in the composition is 6,7-dihydro-4-hydroxy-7-isopropyl-6-oxo-N-(3-(piperidin-1-yl)propyl)thieno[2,3-b]pyridine-5-carboxamide or a pharmaceutically acceptable salt and/or ester thereof.

In an embodiment, the amount of the first compound is sufficient to provide a dosage of less than about 0.25 mg/kg, e.g., between 0.01 and 0.25 mg/kg.

In another embodiment, the first compound may be of the formula

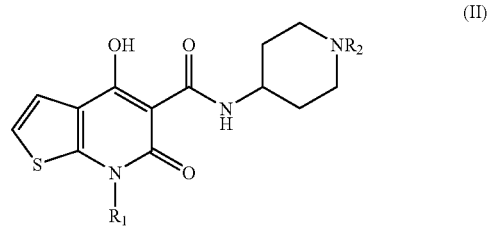

(II)

wherein

R$_1$ may be ethyl or isopropyl; and R$_2$ may be an optionally substituted alkyl group such as ethyl, n-propyl, isopropyl, n-butyl, isobutyl, sec-butyl, pentyl, methylcyclopropyl, isopropanol, phenylethyl; and pharmaceutically acceptable salts and/or esters thereof.

In yet another embodiment, the first compound may be of the formula

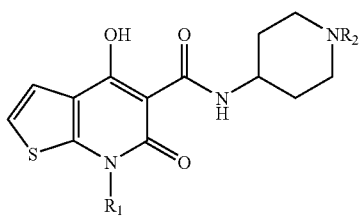

(III)

wherein

R$_1$ may be (C$_1$-C$_8$) branched or unbranched alkyl or alkenyl; a (C$_1$-C$_8$) substituted or unsubstituted carbocyclic ring; a substituted or unsubstituted aryl or heteroaryl ring; branched or unbranched haloalkyl (e.g., CF$_3$, CF$_3$—CH$_2$, CF$_3$—CF$_2$—); or a substituted or unsubstituted (CH$_2$)$_p$-aryl or (CH$_2$)$_p$-heteroaryl ring, where p is 1, 2, 3, or 4; and R$_2$ may be an optionally substituted (C$_1$-C$_6$) branched or unbranched alkyl, alkenyl, alkynyl, alkylhydroxy, alkylalkoxy, or alkylacyl group. Suitable substituents on R$_2$ include substituted or unsubstituted aryl; hydroxyl; (C$_1$-C$_6$) substituted or unsubstituted carbocyclic rings; substituted or unsubstituted (C$_1$-C$_6$)alkylhydroxy, substituted or unsubstituted (C$_1$-C$_6$)alkylalkoxy, substituted or unsubstituted (C$_1$-C$_6$) alkylamino, substituted or unsubstituted (C$_1$-C$_6$)alkylaminoacyl, substituted or unsubstituted (C$_1$-C$_6$)alkylaminoaryl.

Suitable R$_2$ groups include methyl, ethyl, n-propyl, isopropyl, n-butyl, isobutyl, sec-butyl.

Particularly suitable 5-HT$_4$ compounds for use in the combination therapies and compositions of the present invention may be found as disclosed in copending U.S. application Ser. No. 10/955,434, filed on Sep. 30, 2004, and Ser. No. 10/960,769, filed on Oct. 7, 2004.

The second compound, i.e., the cholinesterase or acetylcholinesterase inhibitor, may be metrifonate, neostigmine, physostigmine, pyridostigmine, galantamine/galanthamine, donepezil, tacrine, ambenonium, demarcarium, edrophonium, rivastigmine (Exelon®), phenserine, mentane, or eptastigmine; or pharmaceutically acceptable salts and/or esters thereof.

In an embodiment, the amount of the second compound is sufficient to provide a dosage of less than about 0.5 mg/kg, e.g., between 0.1 and 0.5 mg/kg.

The invention also includes methods of treating Alzheimer's disease or a cognition disorder in a patient in need thereof, comprising administering to a patient in need thereof (e.g., one having been diagnosed as in need of treatment) a therapy including a first compound which is a 5-HT$_4$ modulator and a second compound which is a cholinesterase or acetylcholinesterase inhibitor. The amount of either first or second compound is present in an amount, which if administered alone, does not substantially enhance memory.

In an embodiment, the first compounds are of formulae I, II or III, as noted above. In an embodiment, the amount of the first compound is sufficient to provide a dosage of less than about 0.25 mg/kg, e.g., between 0.01 and 0.25 mg/kg.

The second compound, i.e., the cholinesterase or acetylcholinesterase inhibitor, may be metrifonate, neostigmine, physostigmine, pyridostigmine, galantamine/galanthamine, donepezil, tacrine, ambenonium, demarcarium, edrophonium, rivastigmine (Exelon®), phenserine, mentane, or eptastigmine; or pharmaceutically acceptable salts and/or esters thereof.

In an embodiment, the amount of the second compound is sufficient to provide a dosage of less than about 0.5 mg/kg, e.g., between 0.1 and 0.5 mg/kg.

The invention also includes methods of enhancing memory in a patient in need thereof, comprising administering to a patient in need thereof (e.g., one having been diagnosed as in need of treatment) a therapy including a first compound which is a 5-HT$_4$ modulator and a second compound which is a cholinesterase or acetylcholinesterase inhibitor. The amount of either first or second compound is present in an amount, which if administered alone, does not substantially enhance memory.

In an embodiment, the first compounds are of formulae I, II or III, as noted above. In an embodiment, the amount of the first compound is sufficient to provide a dosage of less than about 0.25 mg/kg, e.g., between 0.01 and 0.25 mg/kg.

The second compound, i.e., the cholinesterase or acetylcholinesterase inhibitor, may be metrifonate, neostigmine, physostigmine, pyridostigmine, galantamine/galanthamine, donepezil, tacrine, ambenonium, demarcarium, edrophonium, rivastigmine (Exelon®), phenserine, mentane, or eptastigmine; or pharmaceutically acceptable salts and/or esters thereof.

In an embodiment, the amount of the second compound is sufficient to provide a dosage of less than about 0.5 mg/kg, e.g., between 0.1 and 0.5 mg/kg.

The first and second compounds may be administered together, or separately.

DETAILED DESCRIPTION OF THE INVENTION

Figure 1:
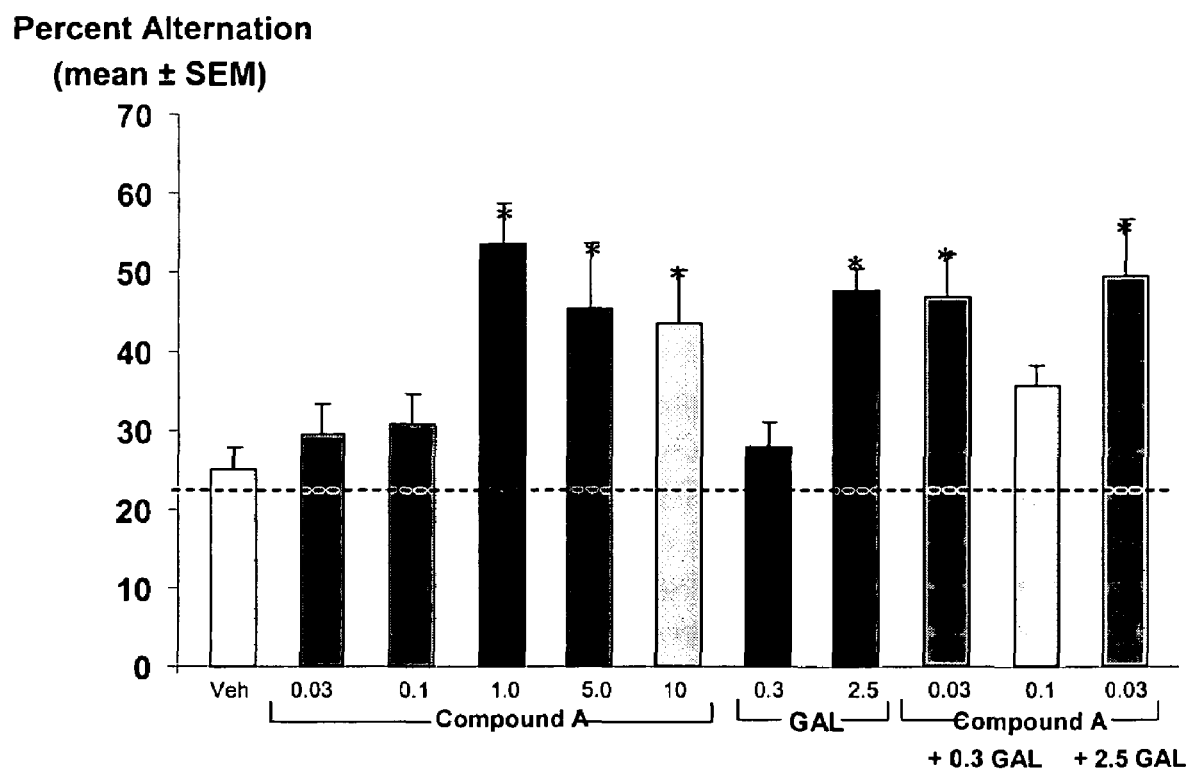
FIG. 1 illustrates data from Example 1 wherein a combination therapy in accordance with the invention is demonstrated in rats. The mean alternation score is presented as the percentage of times a rat successfully visited 4 different arms over 4 consecutive choices or 4 different arms over 5 consecutive choices.

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification, examples, and appended claims are collected here.

"5-HT receptor modulator" or "5-HT modulator" includes compounds having effect at the 5-HT$_1$, 5-HT$_2$, 5-HT$_3$, 5-HT$_4$, 5-HT$_5$, 5-HT$_6$ or 5-HT$_7$ receptors, including the subtypes of each receptor type, such as 5-HT$_{1A, B, C, D, E\ or\ F}$; 5-HT$_{2A, B\ or\ C}$; h5-HT$_{4a, b, c, d\ or\ e}$; and 5-HT$_{5A\ or\ B}$. 5-HT modulators may be agonists, partial agonists, inverse agonists, or antagonists.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure. "$C_1$-$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). A is particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

Compounds of the invention may generally be used in the treatment or prophylaxis of gastrointestinal disorders, cardiovascular disorders and CNS disorders. They are of potential interest in the treatment of irritable bowel syndrome (IBS), in particular the diarrhea aspects of IBS, i.e., these compounds block the ability of 5-HT to stimulate gut motility via activation of enteric neurons. In animal models of IBS, this can be conveniently measured as a reduction of the rate of defecation. They are also of potential use in the treatment of urinary incontinence which is often associated with IBS. They may also be of potential use in other gastrointestinal disorders, such as those associated with upper gut motility, and as anti-emetics. In particular, they are of potential use in the treatment of the nausea and gastric symptoms of gastro-esophageal reflux disease and dyspepsia. Anti-emetic activity is determined in known animal models of cytotoxic-agent/radiation induced emesis.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of formula (I) such as the compounds quaternized by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

$5\text{-HT}_4$ compounds used in the invention may be made as shown in U.S. patent application Ser. No. 10/955,434, which is incorporated herein by reference in its entirety.

Example 1

This example demonstrates that a combination therapy including 6,7-dihydro-4-hydroxy-7-isopropyl-6-oxo-N-(3-(piperidin-1-yl)propyl)thieno[2,3-b]pyridine-5-carboxamide, a partial $5\text{-HT}_4$ receptor agonist and galanthamine hydrobromide, an acetylcholinesterase inhibitor, both in suboptimal doses, enhance delayed spontaneous alternation performance, a yardstick for determining memory enhancement.

In the spontaneous alternation test a rat is allowed to freely explore all arms in the maze. There is no explicit positive reinforcement, e.g., receiving a sweetened cereal piece when entering an arm. Instead, the test takes advantage of a rat's natural exploratory behavior. In particular, the test takes advantage of a rat's bias to choose the least recently visited arm in navigating among a restricted number of arms in a maze (Dember & Fowler, 1958). In order for a rat to choose the least recently visited arm it must remember which arms it entered most recently. Therefore, this task has a short-term or working memory component to it. Several previous studies have also shown that tasks with a central memory component depend on septo-hippocampal cholinergic activity and that modifications to cholinergic activity result in altered memory performance (e.g., Chang & Gold, 2004).

Subjects

Male Long-Evans rats (Charles River Laboratories, Indianapolis, Ind.) weighing between 325 and 375 grams at the time of testing were used for all experiments. Subjects were individually housed in plastic cages in a temperature controlled room with a 12 hour light:dark cycle (lights on a 8:00 h). Rats had free access to food and water except for the 24 hours preceding testing, at which time they were restricted to approximately 12 grams of food. The experiments were conducted in accordance with the United States government principles for the utilization and care of vertebrate animals used in testing, research, and training.

Apparatus

The delayed spontaneous alternation task was tested on a four-arm cross maze made of 0.6 cm thick black plastic. The maze was placed on a table that was 75 cm above the floor. Each arm of the maze was 55 cm long and 10 cm wide that had walls with a height of 15 cm.

| Test substances (name/code) | M.W. | Form |
|---|---|---|
| Compound A (6,7-dihydro-4-hydroxy-7-isopropyl-6-oxo-N-(3-(piperidin-1-yl)propyl)thieno[2,3-b]pyridine-5-carboxamide) | 415.59 | powder |
| Galanthamine Hydrobromide | 368.27 | powder |

Delay Spontaneous Alternation and Drug Injection Procedure

All rats used for this task were naïve. Thirty minutes before testing rats were injected i.p. with Compound A (0.03, 0.1, 1, 5, or 10 mg/kg), galanthamine hydrobromide (0.3 or 2.5 mg/kg), a combination of the two (Compound A 0.03 mg/kg and galanthamine 0.3 mg/kg, Compound A 0.1 mg/kg and galanthamine 0.3 mg/kg, or Compound A 0.03 mg/kg and Galanthamine 2.5 mg/kg), or vehicle (5% DMSO/sterile water). Rats were placed in the testing room five minutes before testing. In the delay version of the spontaneous alternation task, rats were allowed to freely choose an arm, but after making a choice, the rat was blocked into that arm for 30 seconds. After the 30 second delay the block was removed and the rat was free to make another choice. The test session lasted 15 minutes. Rats that did not make 11 or more choices were excluded from the analyses. The number of rats in each group was 6, except the vehicle group (n=15) and the combination of Compound A 0.03 mg/kg and galanthamine 2.5 mg/kg (n=5).

Data Analysis

The following alternation performance was scored for each version of the task:

4/4 alternations: the rat needed to visit each arm once over the course of 4 entries. The number of times that a rat successfully visited 4 different arms during a sequence of 4 entries was used to calculate an alternation score.

Overall number of entries: the overall number of entries was also analyzed to determine if any of the drugs were altering activity levels.

Analysis of Variance was used to determine whether or not there was an overall effect of treatment on the dependent measures. In the case of an overall treatment effect, Fisher's Least Significant Difference (LSD) post-hoc test was used to determine which drugs were significantly different from vehicle.

Results

Delayed Spontaneous Alternation

In the delayed spontaneous alternation test, vehicle control performance was near chance performance (see FIG. 1). Compound A treatment enhanced spontaneous alternation performance in a dose-dependent fashion. In addition, galanthamine hydrobromide also improved alternation scores in a dose-dependent fashion. The analyses indicated that there was a significant effect for treatment on the alternation score, $F(10, 62)=4.964$, $p<0.001$. Fisher's least significant difference post-hoc tests revealed that compared to vehicle controls, Compound A (1, 5, and 10 mg/kg) and galanthamine hydrobromide (2.5 mg/kg) significantly increased delayed alternation scores (p's<0.001). Furthermore, the combination of Compound A at 0.03 mg/kg with galanthamine hydrobromide at 0.3 or 2.5 mg/kg significantly enhanced delayed alternation scores compared to that of vehicle controls (p's<0.001). However, combined Compound A (0.03 mg/kg)/galanthamine (2.5 mg/kg) treatment did not affect delayed spontaneous alternation performance compared to that of galanthamine (2.5 mg/kg) treatment alone (p>0.05). There was essentially a bimodal distribution of scores in the Compound A (0.03 mg/kg)/galanthamine (2.5 mg/kg) group with two rats exhibiting scores greater than 65% and the other three rats exhibiting scores slightly less than 40%.

Arm Entries in Delayed Spontaneous Alternation

Figure 2:
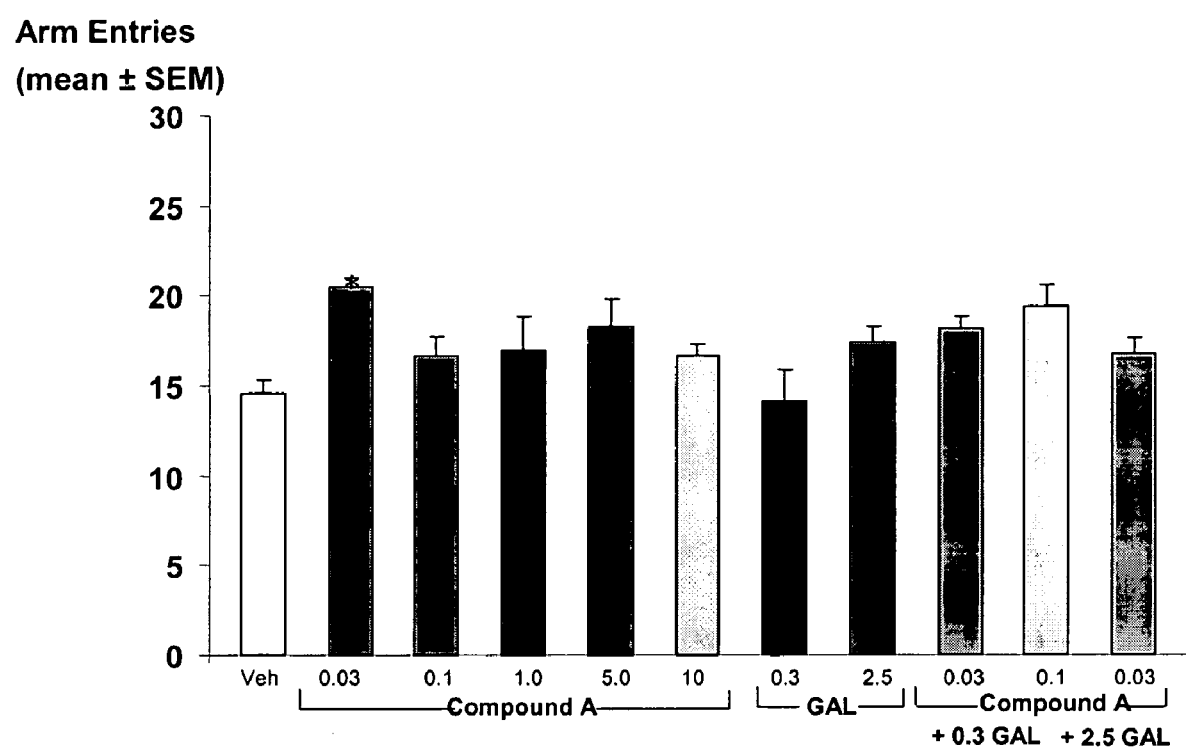
FIG. 2 illustrates data from Example 1, namely, the mean number of arm entries during the 15 minute delay spontaneous alternation session.

The results from the number of arm entries in delayed spontaneous alternation are shown in FIG. 2. The mean number of arm entries among the groups ranged from 14.6 to 20.5. There was an overall effect of drug on the number of arm entries, $F(10, 62)=3.159$, $p<0.01$. Post-hoc tests revealed that only the 0.03 mg/kg Compound A group was significantly different from vehicle.

Conclusions

Compound A facilitates spontaneous alternation performance across a broad range of doses from 1 to 10 mg/kg. In this galanthamine hydrobromide enhanced performance at a dose of 2.5 mg/kg but not 0.3 mg/kg. Furthermore, the combination of suboptimal doses of Compound A and galanthamine hydrobromide also led to memory enhancement, e.g., 0.3 mg/kg of galanthamine hydrobromide combined with 0.03 mg/kg of Compound A improved performance on the delayed spontaneous alternation task.

The low dose of Compound A (0.03 mg/kg) when combined with 2.5 mg/kg of galanthamine hydrobromide did not further enhance delayed spontaneous alternation performance compared to that of galanthamine 2.5 mg/kg treatment alone. However, as described above, two of the five rats exhibited scores that were enhanced compared to that of the galanthamine (2.5 mg/kg) treatment group. One possibility is that a more reliable potentiation of the galanthamine effect with Compound A would be observed if a slightly different combination of doses for Compound A and/or galanthamine was used.

Compound A (0.03 mg/kg) when administered alone significantly increased the number of arm entries. Previous studies have found that certain pharmacological treatments may increase or decrease the number of arm entries in the spontaneous alternation task, however, there is no relationship between the number of arm entries and spontaneous alternation performance. This is the case in this experiment. Despite an increase in the number of arm entries Compound A at 0.03 mg/kg neither increased or decreased spontaneous alternation performance compared to that of vehicle controls. Instead, the research findings indicate that a low dose of Compound A when combined with a low dose of galanthamine enhances working memory.

Example 2

This example demonstrates that suboptimal doses of Compound A and galanthamine in combination enhance spatial memory.

Subjects

Male Long-Evans rats (Charles River Laboratories, Indianapolis, Ind.) weighing between 350 and 400 grams at the time of testing were used for all experiments. Subjects were individually housed in plastic cages in a temperature controlled room with a 12 hour light:dark cycle (lights on a 7:00 h). Rats had free access to food and water except for the 24 hours preceding testing, at which time they were restricted to approximately 12 grams of food. The experiments were conducted in accordance with the United States government principles for the utilization and care of vertebrate animals used in testing, research, and training.

Apparatus

The delayed spontaneous alternation task was tested on a four-arm cross maze made of 0.6 cm thick black plastic. The maze was placed on a table that was 75 cm above the floor. Each arm of the maze was 55 cm long and 10 cm wide that had walls with a height of 15 cm.

Delay Spontaneous Alternation and Drug Injection Procedure

All rats used for this version of the task were naïve. Thirty minutes before testing rats received a single injection of either vehicle (5% DMSO/sterile water), Compound A 0.3 mg/kg, galanthamine 0.3 or 2.5 mg/kg, or a combination of Compound A (0.1 mg/kg)/galanthamine (0.3 mg/kg), Compound A (0.3 mg/kg)/galanthamine (0.3 mg/kg), Compound A (0.3 mg/kg)/galanthamine (0.1 mg/kg). Rats were placed in the testing room 5 minutes before testing. In the delay version, rats were allowed to freely choose an arm, but after making a choice, the rat was blocked into that arm for 30 seconds. After the 30 second delay the block was removed and the rat was free to make another choice. The test session lasted 15 minutes. Rats that did not make 11 or more choices were excluded from the analyses. The number of rats in each group was 4-13.

Data Analysis

The following alternation performance was scored for each version of the task:

4/4 alternations: the rat needed to visit each arm once over the course of 4 entries. The number of times that a rat successfully visited 4 different arms during a sequence of 4 entries was used to calculate an alternation score.

Overall number of entries: the overall number of entries was also analyzed to determine if any of the drugs were altering activity levels.

Results

Vehicle controls had alternation scores of approximately 25%. Galanthamine treatment at 0.3 mg/kg produced alternation scores similar to that of vehicle controls. In contrast, galanthamine treatment at 2.5 mg/kg enhanced delayed alternation performance to approximately 50%. Compound A at 0.3 mg/kg led to slight enhancement of delayed alternation producing alternation scores near 40%. Galanthamine at 0.1 or 0.3 mg/kg in combination with Compound A 0.3 mg/kg had no effect on alternation scores compared to that of Compound A (0.3 mg/kg) treatment alone. The combination of galanthamine 0.3 mg/kg and Compound A 0.1 mg/kg, a dose not found to affect delayed spontaneous alternation, enhances delayed alternation scores (~40%) compared to that of vehicle controls.

High doses of galanthamine (e.g., 2.5 mg/kg) enhances delayed spontaneous alternation, but suboptimal doses of galanthamine (0.3 mg/kg) and Compound A (0.1 mg/kg) together enhance spatial memory.

Example 3

This example demonstrates the effect of much larger doses of Compound A on hippocampal acetylcholine levels in rats during delayed spontaneous alternation.

Subjects

Male Long-Evans rats (Charles River Laboratories, Indianapolis, Ind.) weighing between 350 and 400 grams at the time of testing were used for all experiments. Subjects were individually housed in plastic cages in a temperature controlled room with a 12 hour light:dark cycle (lights on a 7:00 h). Rats had free access to food and water except for the 24 hours preceding testing, at which time they were restricted to approximately 12 grams of food. The experiments were conducted in accordance with the United States government principles for the utilization and care of vertebrate animals used in testing, research, and training.

Apparatus

The delayed spontaneous alternation task was tested on a four-arm cross maze made of 0.6 cm thick black plastic. The maze was placed on a table that was 75 cm above the floor. Each arm of the maze was 55 cm long and 10 cm wide that had walls with a height of 15 cm.

Surgery

Each rat received stereotaxic surgery to implant cannulae into the ventral hippocampus. A rat was first injected with atropine sulfate (0.2 mL; of a 250 μg/mL solution, i.p.). Ten minutes later, sodium pentobarbital (50 mg/kg, i.p.) was administered as a general anesthetic. The rat was then placed in the stereotaxic frame and a mid-saggital incision was made. Each rat was implanted bilaterally with a 10-mm guide cannulae (CMA microdialysis) at stereotaxic coordinates 5.2 posterior to bregma, 5.2±lateral to the midline, and 3.7 ventral to the surface is of the skull. Four jeweler's screws were positioned in the skull surrounding the cannulae and were secured in place with dental acrylic. Following surgery, rats received 3 cc of saline (s.c.). Each rat was fed ground rat-chow with sugar mixed in water for 1 day before returning to the normal diet of rat chow.

Microdialysis Procedure

The day before testing, the rat was placed in a large plastic bowl and a microdialysis probe was inserted into the cannula for 3 min to prevent the possibility of clogging. On the day of testing, a 3-mm dialysis probe (CMA) was inserted through the guide cannula into the hippocampus. The dialysis probe was connected to polyethylene tubing (CMA), which was connected to a quartz swivel (Instech), an additional length of tubing, and then to an infusion pump (Harvard Apparatus). The probe was perfused continuously at a rate of 1.5 μL/min with artificial cerebrospinal fluid, which consisted of 128 mM NaCl, 2.5 mM KCl, 1.3 mM $CaCl_2$, 2.1 mM $MgCl_2$, 0.9 mM $NaH_2PO_4$, 2.0 mM $Na_2HPO_4$, 1.0 mM dextrose and adjusted to pH 7.4 by NaOH. To reliably detect acetylcholine levels in the dialysate, the reversible acetylcholinesterase inhibitor, neostigmine bromide (0.1 μM) was added to the artificial cerebrospinal fluid.

Drug Injection and Spontaneous Alternation with Delay Procedure

On the day of testing, a microdialysis probe was inserted into the hippocampus of a rat and the rat was placed in a large plastic bowl. The first 60 min of perfusate was not analyzed to allow for equilibration between the brain tissue and perfusion solution before testing. Subsequently, samples were collected at 8-min intervals. Three baseline samples were collected, and then rats were injected i.p. with Compound A (1 or 5 mg/kg) or vehicle (5% DMSO/sterile water) with an injected volume of 5 ml/kg. Thus, a rat received an injection with a volume between 1.5-2.0 ml, depending on their weight. Four additional baseline samples were collected and then the rat was placed on the maze to begin spontaneous alternation testing. Thus, the testing session begin thirty-two minutes after receiving the drug or vehicle. In this version of the spontaneous alternation paradigm, rats were allowed to freely choose an arm, but after making a choice, a rat was blocked into that arm for 30 seconds. The block was then removed and a rat was free to make another choice. The test session lasted 16 minutes, during which time two microdialysis samples were collected. After testing was over, rats were returned to the plastic bowl and two posttest samples were collected. Rats that did not make 11 or more choices were excluded from the analyses. The number of rats in each group is 7.

Drug Injection and Resting Condition Procedure

For resting condition measurements, the procedure was identical to the behavioral testing procedure, except the rat was not placed on the maze.

Acetylcholine Assay

Samples (10 µL) were assayed for acetylcholine using high-pressure liquid chromatography with electrochemical detection. Samples were loaded on a microbore analytical column for separation of acetylcholine and choline. Following separation, an enzymatic post-column reactor containing acetylcholinesterase and choline oxidase converted acetylcholine to choline and acetate and choline to betaine and hydrogen peroxide. Acetylcholine and choline were further broken down into stoichiometric quantities of hydrogen peroxide. Hydrogen peroxide was broken down and detected by a glassy carbon wired electrode coated with horseradish peroxidase at +100 mV versus and Ag/AgCk reference electrode. The mobile phase consisted of 50 mM $Na_2HPO_4$, 0.3 mM EDTAm abd 0.005% ProClin was delivered at a rate of 100 µL/min by a solvent delivery system.

Statistical Analysis

The following alternation performance was scored:

4/4 alternations: the rat needed to visit each arm once over the course of 4 entries. The number of times that a rat successfully visited 4 different arms during a sequence of 4 entries was used to calculate an alternation score.

Overall number of entries: the overall number of entries was also analyzed to determine if any of the drugs were altering activity levels.

Microdialysis data was analyzed by converting the raw values to percentages of pre-drug baseline output. The baseline output was calculated from the mean of the first 3 samples for each subject.

Analysis of Variance tests were used to determine whether or not there was an overall effect of treatment on the dependent measures. Post-hoc analyses was employed when there was a significant main effect.

Results

Delayed Spontaneous Alternation

In the delayed spontaneous alternation test, vehicle controls were near chance performance (22%) based on the 4/4 criterion. Compound A treatment at both the 1 and 5 mg/kg dose enhance delayed spontaneous alternation performance to approximately 45%. The difference in spontaneous alternation scores among the groups was significant, $F (2,20)=12.30$, $p<0.01$. Post-hoc analyses indicated that alternation scores were significantly greater in the Compound A groups compared to that of vehicle controls ($p$'s$<0.01$).

Arm Entries in Delayed Spontaneous Alternation

The mean number of arm entries among the groups ranged from 11-22. The difference in the number of arm entries among the groups was not statistically significant, $F (2, 20)=0.14$, $p>0.05$.

Acetylcholine Output During Delayed Spontaneous Alternation

Acetylcholine efflux in the hippocampus was at similar levels in rats receiving vehicle and Compound A 1 mg/kg or 5 mg/kg during the post-drug baseline, although output was consistently higher in rats receiving Compound A. In the first 8 minutes of delayed spontaneous alternation, acetylcholine efflux increased approximately 35% above basal levels in controls rats and approximately 65% above basal levels in the two drug groups. In the final 8 minutes, acetylcholine output increased to 60% above basal levels in control rats and approximately 110% in both drug groups. Analysis of variance with repeated measures revealed there was a main effect for time, $F (8, 160)=66.32$, $p<0.01$ and a significant time by treatment interaction, $F (16, 160)=1.91$, $p<0.05$. Post-hoc analyses of the time x treatment interaction indicated that hippocampal ACh output during the last 8 minutes of testing was significantly greater in the Compound A treatment groups compared to that of vehicle controls ($p<0.05$).

Acetylcholine Output During Resting Condition

Acetylcholine output in the hippocampus was no different in rats receiving vehicle or Compound A 1 or 5 mg/kg. There was a slight increase in ACh output in all groups immediately following an injection which gradually reverted to baseline levels at similar rates.

Enhanced spontaneous alternation performance with Compound A is accompanied by increased hippocampal acetylcholine output. Compound A influence on hippocampal ACh output only occurred in the delayed spontaneous alternation. This task itself enhanced hippocampal ACh output in controls. The increase in hippocampal ACh output during delayed spontaneous alternation was potentiated by Compound A treatment. In a resting condition, Compound A had no effect on hippocampal ACh output. The findings suggest that Compound A modulates hippocampal ACh output under conditions that engage the hippocampal cholinergic system.

The facilitation of delayed spontaneous alternation performance with Compound A administration along with the current data showing enhanced acetylcholine release indicates that the treatment enhances short-term or working memory processes by enhancing cholinergic activity.

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A pharmaceutical composition comprising
a first compound of the formula

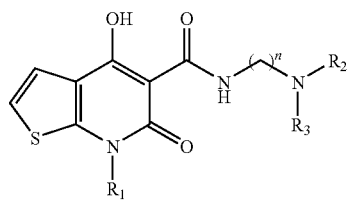

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$-aryl, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof; the first compound being present in an amount which if administered alone does not substantially enhance memory; and a second compound which is a cholinesterase or acetylcholinesterase inhibitor and is present in an amount which if administered alone does not substantially enhance memory.

2. The pharmaceutical composition of claim 1, wherein $R_1$ is a ($C_1$-$C_8$) alkyl selected from the group consisting of methyl, ethyl, isopropyl, n-propyl, n-butyl or isobutyl; $R_2$ and $R_3$ taken together form a substituted or unsubstituted piperidine (N-containing six-membered cyclic ring); and n is 3.

3. The pharmaceutical composition of claim 1, wherein the branched or unbranched haloalkyl group contains a halogen atom selected from the group consisting of F, Cl, Br, and I.

4. The pharmaceutical composition of claim 1, wherein the first compound is 6,7-dihydro-4-hydroxy-7-isopropyl-6-oxo-N-(3-(piperidin-1-yl)propyl)thieno[2,3-b]pyridine-5-carboxamide or a pharmaceutically acceptable salt and/or ester thereof.

5. The pharmaceutical composition of claim 1, wherein the amount of the first compound is sufficient to provide a dosage of less than about 0.25 mg/kg.

6. The pharmaceutical composition of claim 1, wherein the amount of the first compound is sufficient to provide a dosage of between 0.01 and 0.25 mg/kg.

7. The pharmaceutical composition of claim 1, wherein the second compound is selected from the group consisting of metrifonate, neostigmine, physostigmine, pyridostigmine, galantamine/galanthamine, donepezil, tacrine, ambenonium, demarcarium, edrophonium, rivastigmine, phenserine, mentane, and eptastigmine; or pharmaceutically acceptable salts and/or esters thereof.

8. The pharmaceutical composition of claim 1, wherein the amount of the second compound is sufficient to provide a dosage of less than about 0.5 mg/kg.

9. The pharmaceutical composition of claim 1, wherein the amount of the second compound is sufficient to provide a dosage of between 0.1 and 0.5 mg/kg.

10. A method of treating Alzheimer's disease in a patient in need thereof, comprising administering to a patient in need thereof a therapy including a first compound having the formula

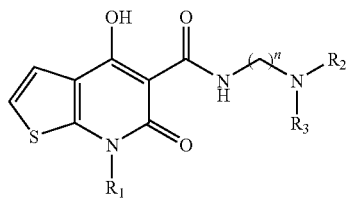

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$-aryl, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof; and a second compound which is a cholinesterase or acetylcholinesterase inhibitor and is present in an amount which if administered alone does not substantially enhance memory.

11. A method of enhancing memory in a patient in need thereof, administering to a patient in need thereof a therapy including a first compound having the formula

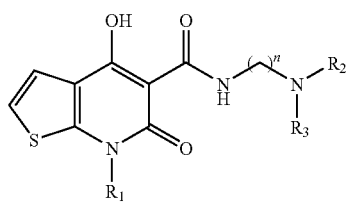

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$-aryl, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof; and a second compound which is a cholinesterase or acetylcholinesterase inhibitor and is present in an amount which if administered alone does not substantially enhance memory.

12. A method of treating Alzheimer's disease in a patient in need thereof, comprising diagnosing a patient in need of treatment and administering to a patient in need thereof a therapy including a first compound having the formula

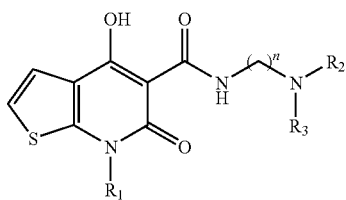

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof, the first compound being present in an amount which if administered alone does not substantially enhance memory; and a second compound which is a cholinesterase or acetylcholinesterase inhibitor and is present in an amount which if administered alone does not substantially enhance memory.

13. A method of enhancing memory in a patient in need thereof, comprising diagnosing a patient in need of treatment and administering to a patient in need thereof a therapy including a first compound having the formula

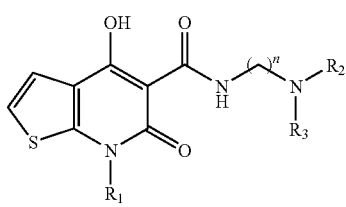

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$-aryl, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof, the first compound being present in an amount which if administered alone does not substantially enhance memory; and a second compound which is a cholinesterase or acetylcholinesterase inhibitor and is present in an amount which if administered alone does not substantially enhance memory.

14. The method of any one of claims 10, 11, 12 or 13; wherein the first and second compounds are administered together.

15. The method of any one of claims 10, 11, 12 or 13, wherein the first and second compounds are administered separately.

16. The method of any one of claims 10, 11, 12 or 13, wherein the amount of the first compound is sufficient to provide a dosage of less than about 0.25 mg/kg.

17. The method of any one of claims 10, 11, 12 or 13, wherein the amount of the first compound is sufficient to provide a dosage of between 0.01 and 0.25 mg/kg.

18. The method of any one of claims 10, 11, 12 or 13, wherein the amount of the second compound is sufficient to provide a dosage of less than about 0.5 mg/kg.

19. The method of any one of claims 10, 11, 12 or 13, wherein the amount of the second compound is sufficient to provide a dosage of between 0.1 and 0.5 mg/kg.

20. A pharmaceutical composition comprising a first compound of the formula

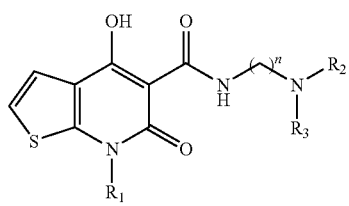

wherein $R_1$ is ($C_1$-$C_8$) branched or unbranched alkyl; a ($C_1$-$C_8$) substituted or unsubstituted carbocyclic ring; branched or unbranched haloalkyl, a substituted or unsubstituted aryl, or a substituted or unsubstituted $(CH_2)_p$-aryl, where p is 1, 2, 3, or 4; $R_2$ and $R_3$, taken together, form a substituted or unsubstituted piperidine, pyrrolidine, azepane, aziridine, or azetidine ring; and n is 1, 2, 3, 4, 5 or 6; and pharmaceutically acceptable salts and/or esters thereof; and a second compound which is a cholinesterase or acetylcholinesterase inhibitor, the first or second compound being present in an amount, which if administered alone, does not substantially enhance memory.

21. The pharmaceutical composition of claim 20, wherein the first compound is 6,7-dihydro-4-hydroxy-7-isopropyl-6-oxo-N-(3-(piperidin-1-yl)propyl)thieno[2,3-b]pyridine-5-carboxamide or a pharmaceutically acceptable salt and/or ester thereof.

22. The pharmaceutical composition of claim 20, wherein the amount of the first compound is sufficient to provide a dosage of less than about 0.25 mg/kg.

23. The pharmaceutical composition of claim 20, wherein the second compound is selected from the group consisting of metrifonate, neostigmine, physostigmine, pyridostigmine, galantamine/galanthamine, donepezil, tacrine, ambenonium, demarcarium, edrophonium, rivastigmine, phenserine, mentane, and eptastigmine; or pharmaceutically acceptable salts and/or esters thereof.

24. The pharmaceutical composition of claim 20, wherein the second compound is donepezil or pharmaceutically acceptable salt and/or ester thereof.

25. The pharmaceutical composition of claim 20, wherein the amount of the second compound is sufficient to provide a dosage of less than about 0.5 mg/kg.

* * * * *